US010786382B2

(12) United States Patent
Shagdar et al.

(10) Patent No.: US 10,786,382 B2
(45) Date of Patent: Sep. 29, 2020

(54) MULTIFUNCTIONAL VEST FOR POSTURE CORRECTING, PAIN RELIEVING AND WORKOUT BOOSTING

(71) Applicants: Jargalsaikhan Shagdar, Ulaanbaatar (MN); Odonchimeg Myagmar, Ulaanbaatar (MN)

(72) Inventors: Jargalsaikhan Shagdar, Ulaanbaatar (MN); Odonchimeg Myagmar, Ulaanbaatar (MN)

(*) Notice: Subject to any disclaimer, the term of this patent is extended or adjusted under 35 U.S.C. 154(b) by 420 days.

(21) Appl. No.: 15/672,439

(22) Filed: Aug. 9, 2017

(65) Prior Publication Data

US 2017/0354530 A1    Dec. 14, 2017

Related U.S. Application Data

(60) Provisional application No. 62/412,820, filed on Oct. 25, 2016.

(51) Int. Cl.

| A61F 5/02 | (2006.01) |
|---|---|
| A61B 5/11 | (2006.01) |
| A41D 13/05 | (2006.01) |
| A63B 23/02 | (2006.01) |
| A41D 13/00 | (2006.01) |
| A63B 21/00 | (2006.01) |

(52) U.S. Cl.
CPC .......... *A61F 5/026* (2013.01); *A41D 13/0015* (2013.01); *A41D 13/0525* (2013.01); *A61B 5/1116* (2013.01); *A63B 23/02* (2013.01); *A63B 21/4009* (2015.10)

(58) Field of Classification Search
CPC ........ A61F 5/026; A61F 5/05808; A61F 5/37; A61F 5/028; A61F 5/03; A61F 13/14; A63B 23/02; A63B 21/4009; A63B 23/0205; A63B 23/0216; A63B 23/0233; A63B 23/0238; A63B 21/4007; A63B 21/4005; A41D 13/0015; A41D 13/0525; A41D 13/0007; A41D 13/088; A61B 5/1116; A62B 35/00
USPC .......................................................... 602/19
See application file for complete search history.

(56) References Cited

U.S. PATENT DOCUMENTS

| 5,007,412 A | * | 4/1991 | DeWall | ............... | A41D 13/0531 |
| | | | | | 602/19 |
| 5,328,398 A | * | 7/1994 | Aubrey | ............... | A41D 13/0125 |
| | | | | | 441/106 |

(Continued)

*Primary Examiner* — Tarla R Patel (57) ABSTRACT

A multifunctional vest for posture correcting, pain relieving and workout boosting comprises a vest-like garment wearing by an individual on the torso, the garment having shoulder and waist bands that join the anterior portion with posterior portion for securing and adjusting the fit of the garment to the wearer. The upper anterior section is made of elastic materials that allow for both female and male individuals to wear. The multifunctional vest also comprises removable parts that can be used for multiple purposes. Support stays and scapular straps are provided in the posterior portion for improving body posture. A therapeutic magnet belt that can be attached to both anterior and posterior portion is provided for purpose of relieving pain. For boosting workout purpose, a workout boosting sheet is provided in attaching to necessary place while doing exercise or daily activities.

17 Claims, 9 Drawing Sheets

(56) References Cited

U.S. PATENT DOCUMENTS

| | | | | |
|---|---|---|---|---|
| 6,146,324 | A * | 11/2000 | Engel | A61N 2/008 600/15 |
| 6,478,759 | B1 * | 11/2002 | Modglin | A61F 5/028 128/100.1 |
| 7,396,272 | B1 * | 7/2008 | Newlen | A41D 13/1245 2/114 |
| 7,628,675 | B2 * | 12/2009 | Staub | A41C 3/0057 2/102 |
| 7,922,682 | B2 * | 4/2011 | Bell | A41C 3/0064 128/874 |
| 8,376,808 | B2 * | 2/2013 | Hopkins | A41C 3/08 450/30 |
| 8,870,624 | B2 * | 10/2014 | Hopkins | A41C 3/08 450/31 |
| 9,456,639 | B2 * | 10/2016 | Aylward | A41D 27/205 |
| 2008/0045873 | A1 * | 2/2008 | Zours | A61F 5/026 602/19 |
| 2010/0121240 | A1 * | 5/2010 | Smith | A61F 5/022 602/19 |
| 2010/0204630 | A1 * | 8/2010 | Sandifer | A61F 5/026 602/19 |
| 2012/0059297 | A1 * | 3/2012 | Newkirk | A61F 5/026 602/19 |
| 2012/0245501 | A1 * | 9/2012 | Rossi | A61F 5/026 602/19 |
| 2012/0316483 | A1 * | 12/2012 | Waeger | A61F 5/026 602/19 |
| 2013/0090585 | A1 * | 4/2013 | Bue, Jr. | A61F 5/028 602/19 |
| 2015/0342329 | A1 * | 12/2015 | Formosa | A41F 9/002 224/666 |
| 2016/0074201 | A1 * | 3/2016 | Williamson | A61F 5/028 602/19 |
| 2016/0235129 | A1 * | 8/2016 | Jackson | A41D 31/12 |

* cited by examiner

MULTIFUNCTIONAL VEST FOR POSTURE CORRECTING, PAIN RELIEVING AND WORKOUT BOOSTING

CROSS-REFERENCE TO RELATED APPLICATIONS

The present application claims the benefit of priority to the U.S. Provisional Patent Application of the same title that was filed on Oct. 25, 2016, having application Ser. No. 62/412,820, and is incorporated herein by reference.

BACKGROUND OF THE INVENTION

1. Field of the Invention

The present invention relates to a garment, and in particular, to a vest-like garment that can be used for multiple purposes such as posture correcting, pain relieving and workout boosting.

2. Description of the Prior Art

Because of modern technology, many people need to sit for a long period of time and some people, especially young people has getting wrong body shape, such as pony back, loose shoulder or not strait backbone. And these bad habits may affect not only for their beauty and appearance, but also affect their health condition and may become a potential reason of further severe back problems and overweight.

Many of the prior art tried to resolve these problems, but most of them focused on a sole usage. For example, U.S. Pat. Nos. 3,116,735 and 9,168,167 disclosed a posture brace and posture improvement device, U.S. Pat. No. 4,756,306 and U.S. Pat. No. 20070208288 disclosed a therapeutic belt and therapeutic treatment apparatus, while U.S. Pat. No. 20160235129 disclosed an exercise garment.

Generally, a vest-like garment is well known in the art. However, they are differentiated one another by their figure, material and/or purpose. For instance, there are a number of garment for posture correcting including upper and lower back. Such garments typically comprise a vest with or without sleeves and attachable moving parts such as support stays and scapular straps. By way of example, note US. Pat. No. 20120059297 to Newkirk directed to a scapula-spinal stabilizer with abdominal support for opening the superior thoracic aperture. A device of this type is also shown in U.S. Pat. No. 6,440,094 to Maas. A similar device but for use with a pad or the like to be held in the center of the back is shown in U.S. Pat. No. 9,168,167 to Brown.

People believe that posture correcting garment can help to relieve pain of wearer. That is true in long run, if you use it for a long period of time. But as for an immediate method, there are numerous medical conditions to relieve the pain and discomfort. One of them is magnetotherapy and there are multiple documents wherein a variety of devices or items containing magnets are described and recommended for treating, preventing or improving diverse health conditions. Shimiyashu U.S. Pat. No. 4,480,596, Smith et al., U.S. Pat. No. 6,623,419 as well as Martello U.S. Pat. No. 6,551,234 and Getek U.S. Pat. No. 6,406,418 are examples of US patents wherein therapeutic magnets belts are used in order to reduce musculoskeletal pain, counteract fat or reducing muscles stiffness by exposing the described body areas to magnetic flux.

Similarly, U.S. Pat. No. 6,632,168 to Roberts et al., discloses a magnetic therapeutic device and a method to treat pain or injury areas comprising the use of the said magnetic device under the wearer's skin. Also, there are everyday use articles such as pads, bands, patches, bandages and wrapping materials comprising magnetic items and directed to the magnetotherapy of different parts of the body are disclosed in multiple U.S. Patents such as Juster et al., U.S. Pat. No. 6,344,021, Engel U.S. Pat. No. 6,146,324, Nagler U.S. Pat. No. 6,093,143, Snider U.S. Pat. No. 5,336,498, Russell U.S. Pat. No. 5,782,743 and Griffin et al U.S. Pat. No. 4,587,956 among others.

However, all these prior art is dedicated for only pain relieving purpose. Thus, in accordance with the principle of the present invention, a therapeutic magnet belt adapted for pain relieving placement of the bodies of persons who have previous back problems or abdominal muscle injury, as well as to help preventing the reoccurrence of such problems is provided as one of preferred embodiments of the invention.

Over the years, a lot of weight-loss technologies and methods are introduced on the market, and one of the most effective and popular methods of losing weight is sweating off either through exercise or other available methods. Since a lot of exercise is required for one to sweat-off, a variety of exercise clothing or sportswear that help the users to sweat off with as the least amount of exercise as possible, preventing the air and moisture from coming out of the body of the users, have been introduced on the market. Examples of such prior art exercise garments are described in U.S. Pat. No. 8,732,862 to Shields, U.S. Pat. No. 8,376,808 to Hopkins and U.S. Pat. No. 5,700,231 to Wilkinson. However, such kinds of sportswear or exercising clothing cover the whole or most part of the body of the user as an outwear to achieve a high weight-loss effect so that they cannot wear them during their normal activities or at their work.

From other side, many individuals find that it is difficult to reduce flabbiness on specific body parts, such as abdominal area or waistline. Various garments have been designed for use to increase perspiration and cause weight reduction. Prior art garments of this type are exemplified by those disclosed in U.S. Pat. No. 20140059735 to Taylor and U.S. Pat. No 20110314590 to Perron et al. These garments include a sleeve having top and bottom ends that can be placed around the targeted body area and a pant covering the lower abdomen, crotch and buttocks that cause movement resistance and induce muscle toning and caloric. Again, all of them are focusing on exercise or weight loss purpose only.

So that, the multifunctional vest according to the invention also intends to provide a device that is useful for training aid that provide the general advantages of being a garment that is easy to use and adjust for specific needs, as well as to provide the user with a normal appearance.

It is obvious, once have one problem, there is highly possibility of coming other problems. For example, if someone has a wrong posture, they can suffer from back pain sooner. Or if someone has back pain, of course fat body will make it worse. However, in view of the foregoing, it is clear that aforementioned prior arts couldn't resolve these problems in complex for preventing, correcting and curing purpose.

In this respect, the multifunctional vest according to the invention substantially departs from the conventional concepts, purpose and designs of the prior art, and in doing so provides an one-piece garment primarily developed for the multiple purposes by easily changing given embodiments such as support stays, scapular straps, a therapeutic magnet belt and a workout boosting sheet. Thus, the present invention can readily be adapted for use by individual which need not only the benefit of the posture correcting or pain relieving including prevention of back injury, but also need a workout boosting sheet to keep fit while doing daily activities or exercise.

SUMMARY OF THE INVENTION

Briefly described, the present invention is a versatile, vest-like garment having a front opening that is closed by a zipper. Further, the anterior portion has upper section which is made of expansible material for supporting wearer's breast and chest that is suitable for both men and women wearing. The garment also includes multiple bands that join the anterior portion with the posterior portion. The bands are made of sturdy elastic material that has a strong stretch. An adjustable self-gripping mechanism—hook and loop fastener is provided on each band in order to facilitate the size adjustment for the individual's size as well as comfort for compression level the individual desires.

The multifunctional vest according to the invention attempts to provide an one-piece garment that can be adapted for multiple purposes such as posture correcting, pain relieving and workout boosting by installing given embodiments.

In a preferred embodiment, the multifunctional vest includes two vertical support stays that is disposed in dual sheaths in the posterior panel of the garment. The garment also includes removable scapular straps that are operatively connected to the shoulder and waist bands by crossing over the posterior panel of the garment. Both embodiments are provided for purpose of improving body posture.

In another preferred embodiment, the multifunctional vest includes a therapeutic magnet belt which is provided for purpose of relieving pain. The therapeutic magnet belt can be attached to both anterior portion and posterior portion where the linear strips with hook and loop fasteners are provided.

In another preferred embodiment, the multifunctional vest also includes a workout boosting sheet which is provided for purpose of boosting workout. The workout boosting sheet keeps the body warm and heat up the core abdominal area and other targeted area where the linear strips with hook and loop fasteners are provided while doing exercise or daily activities.

These and other features and advantages of the invention will become more apparent upon reading the following specification in conjunction with the accompanying drawing figures.

BRIEF DESCRIPTION OF THE DRAWINGS

The multifunctional vest according to the invention is described with reference to the accompanying drawings which show preferred embodiments according to the invention described herein. It will be noted that the garment as disclosed in the accompanying drawings is illustrated by way of example only. The various elements and combinations of elements described below and illustrated in the drawings can be arranged and organized differently to result in embodiments which are still within the spirit and scope of the invention described herein.

DETAILED DESCRIPTION OF THE DRAWINGS

Referring now in more detail to the exemplary drawings for purposes of illustrating embodiments of the invention, wherein like reference numerals designate corresponding or like elements among the several views.

Figure 1:
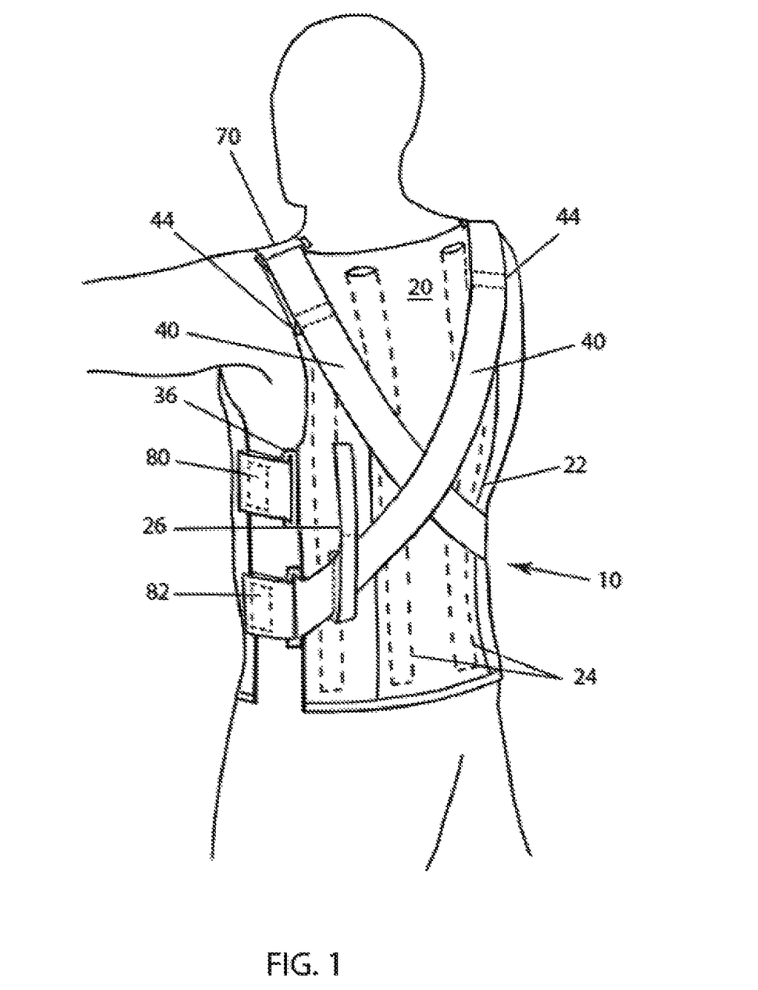
FIG. 1 is a rear elevation view of a multifunctional vest, according to the invention shown being worn by an individual.
Figure 2:
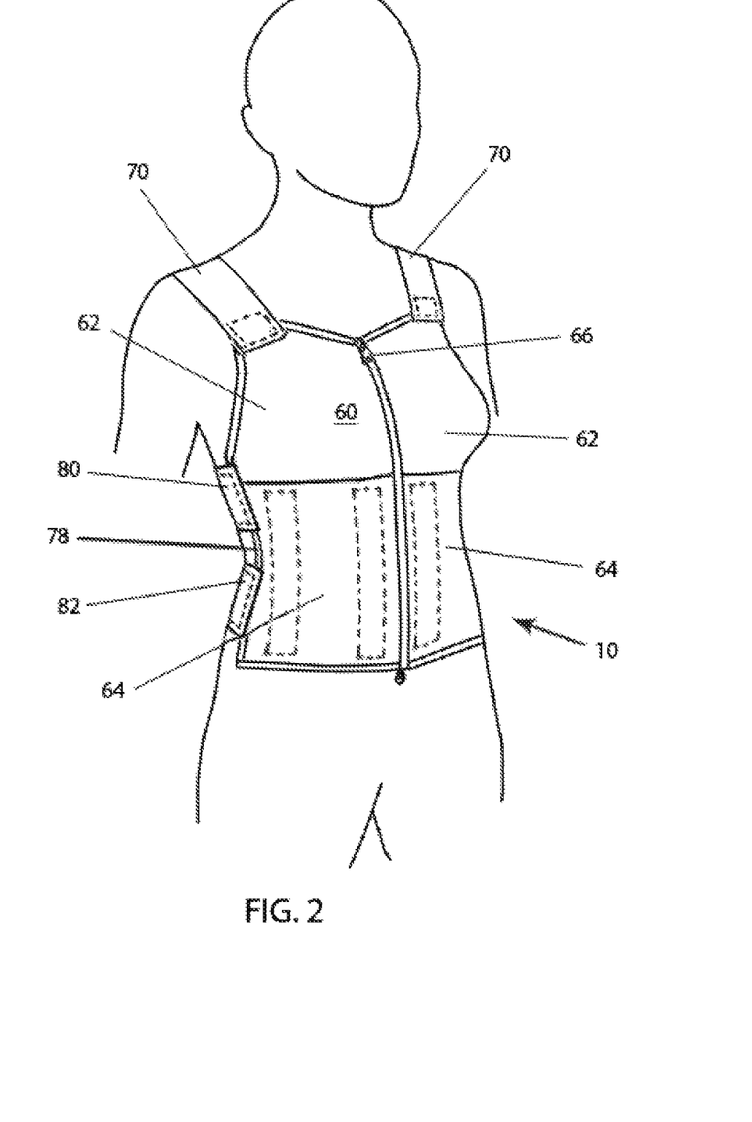
FIG. 2 is a front elevation view of the multifunctional vest shown in FIG. 1 being worn by a woman with zipper closed.

In accordance with the present invention, a multifunctional vest 100 for posture correcting, pain relieving and workout boosting is described, comprising a vest-like garment 10 covering the torso. As shown in FIGS. 1 and 2, a vest-like garment 10 wearing by a male and female individual includes an anterior portion 60 and a posterior portion 20 that are connected each other on shoulder and waist area by at least two or more elasticized bands 70, 80, 82 to form a continuous covering around the wearer's torso.

The posterior portion 20 of the garment 10 extending between the cervical spine and the lumbosacral spinal region, is composed of non-elastic breathable fabric. As shown in FIG. 1, two extendable posterior scapular straps 40 in the posterior portion 20 that simultaneously cross the back and two thoraco-lumbar support stays, as will be described further below, are provided respectively in order to maintain the upper and lower back as well as shoulders of an individual in a correct posture position, especially when the individual is performing repetitive motions for a long period of time in sitting or standing position.

According to the FIG. 2, the garment 10 is provided an opening 76 that is closed by a zipper 66 at the front. Further, the anterior portion 60 has an upper section 62 which is shaped at their upper inner edges to form a (front) V-neck opening 50 for a wearer's neck and head, is made of expansible material for supporting wearer's breast and chest area that is suitable for both men and women wearing. The anterior portion 60 also has a lower section 64 that is formed of non-expansible material which may be same as used in the posterior portion 20, extends below the upper section 62 substantially to the hips of the wearer of the garment 10.

Height adjusting shoulder bands 70 are provided for adjustably connecting the anterior portion 60 with the posterior portion 20 of the garment 10 by extending over the wearer's shoulder. At least two waist bands 80, 82 are provided for the circumference size adjustment by encircling a portion of a wearer's body connecting the anterior portion 60 with the posterior portion 20 of the garment 10. The shoulder and waist bands 70, 80, 82 are preferably composed of a sturdy elastic material that has a strong stretch.

An adjustable self-gripping mechanism, hook and loop fasteners, such as VELCRO™, etc., is provided on each band 70, 80, 82 in order to facilitate the size adjustment for the individual's size as well as comfort for compression level the individual desires.

Figure 3:
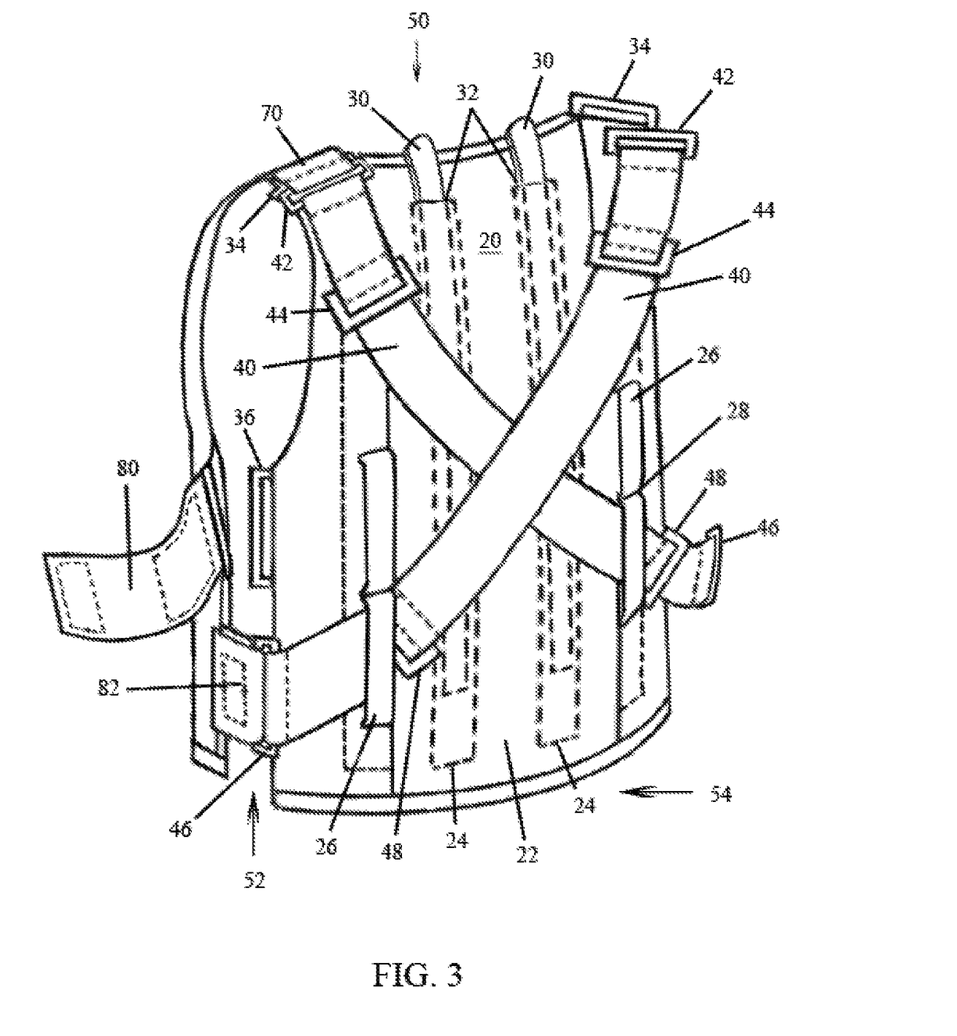
FIG. 3 is an exploded rear upper perspective view of the multifunctional vest shown in FIGS. 1 and 2 with posterior embodiments attached partially.

FIG. 3 illustrates the rear perspective view of the garment 10 showing the way of attaching some embodiments. The embodiment includes two removable support stays 30 and scapular cross straps 40.

A posterior panel 22 extending from the neck opening 50 until the hip opening 54 is provided in the posterior portion 20 in order to create a pocket or a sheath 24 for an embodiment. A pair of vertical, parallel, semi-rigid thoraco-lumbar support stays 30 is disposed in dual sheaths 24 in a posterior panel 22 of the garment 10.

Additionally, two removable scapular straps 40 which are detachably attached by a connector 42 secured at the first end of the strap 40, extending from the shoulder area angularly downward, each strap 40 crossing the other to form an X-shaped configuration as seen in FIGS. 1 and 3, toward the opposite side of the garment 10 where its distal end with a connector 46 is detachably connected to the waist area, as illustrated greatly in detail in FIGS. 6 and 8. Each strap 40 passes through an elongate positioning loop 26 that helps keep straps 40 in relative position across the back of the garment 10. Additional connectors 44 and 48 are provided adjacent to the first and distal end of the straps 40 to facilitate adjusting the straps 40 independently depending on the size and comfort needs of the wearer. See FIG. 6.

Figure 4:
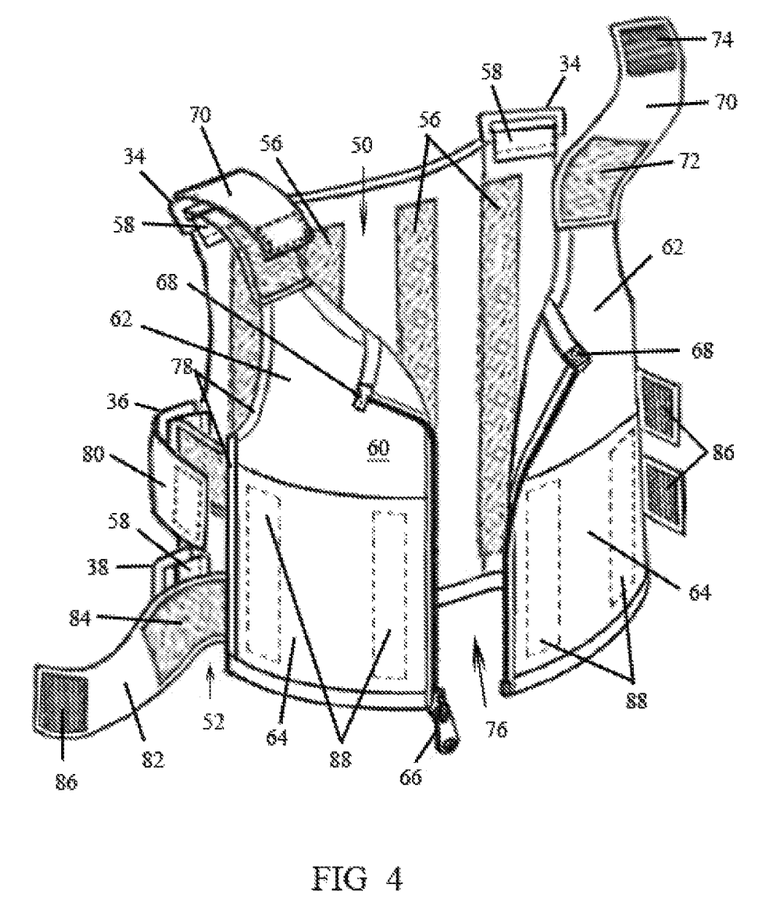
FIG. 4 is an exploded front perspective view of the multifunctional vest shown in FIG. 2 with the front zipper open, exposing the interior anterior portion of the garment.

As shown in FIG. 4, the front perspective view of the garment 10 with a zipper open as well as a shoulder band 70 and a waist band 82 released from the connectors 34 and 38 is illustrated in order to show the inner surface of the bands as well as some interior anterior embodiments. It will be recognized that the other bands 70, 80, 82 can be the same as bands shown in the figure.

The anterior portion 60 includes upper front section 62 and lower front section 64 that are integrally sewn with each other in horizontal direction. The front opening 76 of the garment 10 can be closed by means two fastening elements 66 and 68 of the self-sliding-type, and/or snap buttons, etc., on each side of its opening 76. In an example, two parts of the anterior portion 60 are joined together by a zipper 66 which forms a front closure in the anterior portion 60 of the garment 10. See FIGS. 7 and 9, also. Further, a snap button 68 is provided on the top end of the zipper 66 at the upper front section 62 to facilitate a zipper 66 for holding closed the front opening 76.

The two upward extensions on the upper front section 62 form a front neck opening 50 that is below the top of the posterior portion 20 allow a wearer for comfort in any circumstances including doing exercise and/or workout.

A pair of elongate shoulder bands 70 extending from the upper front section 62 is adapted to extend over a wearer's shoulders to support and to properly position the garment 10 on the wearer's torso. At least two pairs of waist bands 80 and 82 provided on the waist opening 52 of the anterior portion 60 facilitate to connect the anterior portion 60 with the posterior portion 20 by reducing the circumferential size of the garment 10. The shoulder and waist bands 70, 80, 82 are integrally sewn in the neck opening 50 and waist opening 78, respectively, of the anterior portion 60.

Figure 6A:
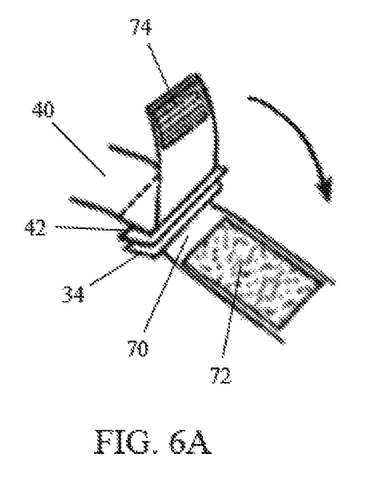
FIGS. 6A and 6B are partially enlarged operational perspective views showing a hook and loop fastener assembly of a shoulder band and a connecting method of a scapular strap thereto, in adjustable way.
Figure 6B:
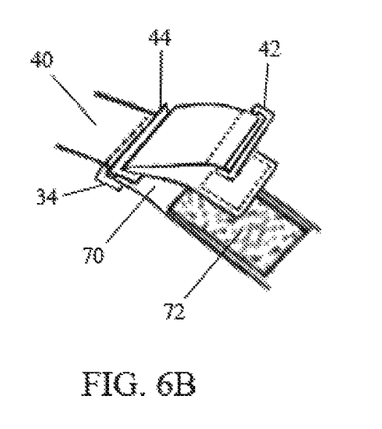
Figure 6C:
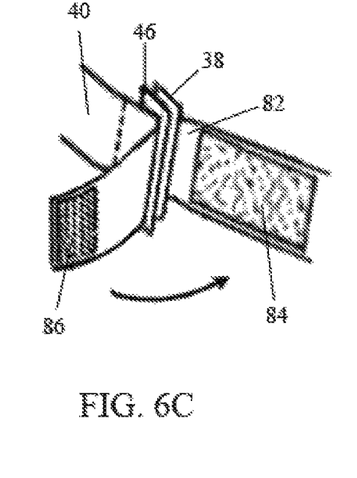
FIGS. 6C and 6D are partially enlarged operational perspective views showing a hook and loop fastener assembly of a waist band and a connecting method of a scapular strap thereto, in adjustable way.
Figure 6D:
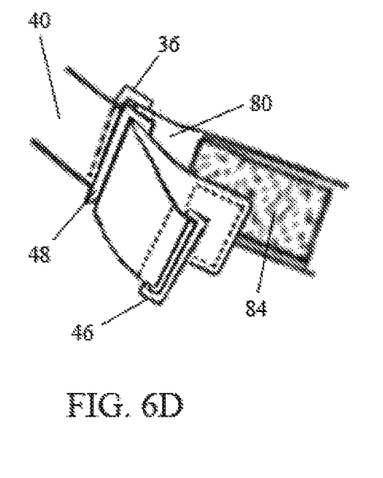
Figure 7:
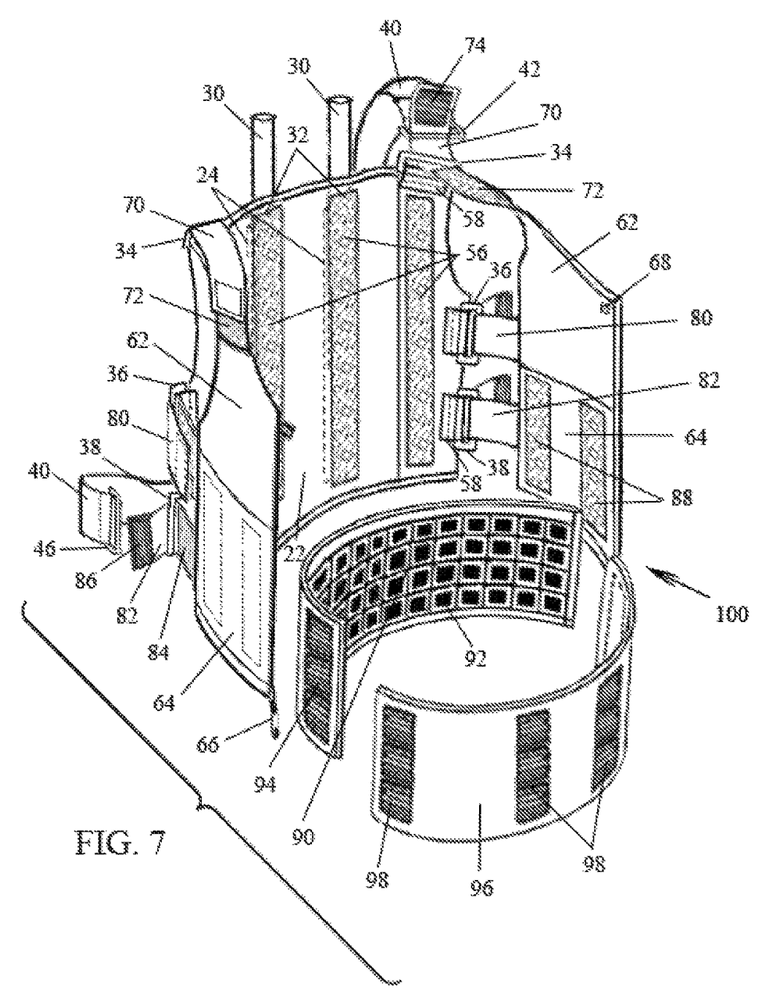
FIG. 7 is a further exploded front upper perspective view of the multifunctional vest similar to FIG. 4, but with fully opened front closure exposing the interior posterior and anterior portions, without assembling the removable embodiments according to the present invention.
Figure 9A:
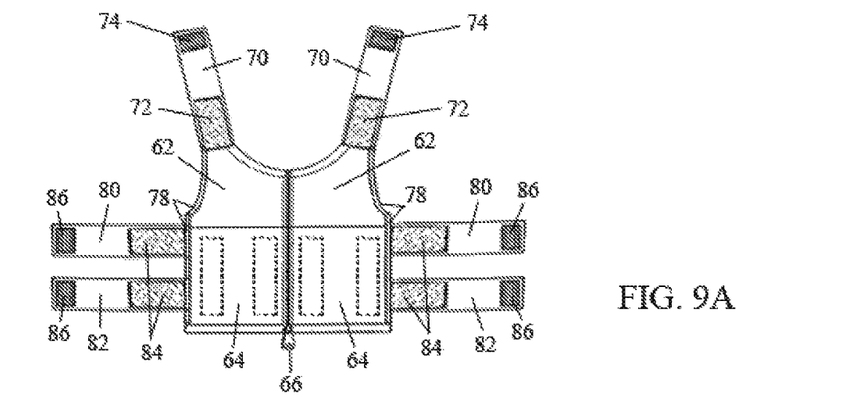
FIG. 9A is a plan view of the multifunctional vest showing its exterior configuration of the front portion closed by a zipper.

An adjustable fastener assembly 72, 74, 84, 86 that is disposed on the outer surface of each band 70, 80, 82, as best seen in FIGS. 6, 7 and 9, forms an integral part of the bands 70, 80, 82 for adjustable engagement over the shoulder and around the waist, respectively, of a wearer. In use, a free end of a band 70, 80, 82 is inserted through the center of the aperture of connectors 34, 36, 38 that fixed in the posterior portion 20 of the garment 10, and doubled outwardly back for adjustably touching to the body of the band 70, 80, 82 itself.

All removable components are illustrated in detail in FIG. 5.

Figure 5A:
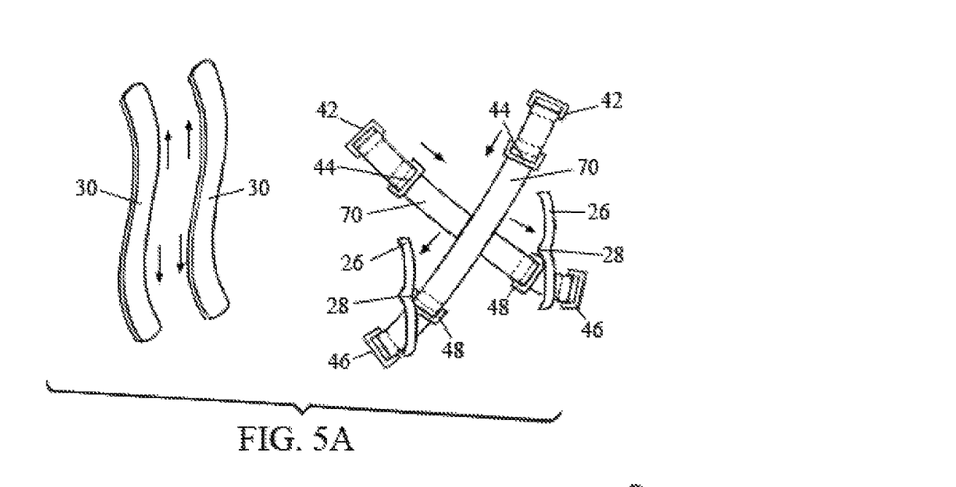
FIG. 5A is an exploded upper perspective view of the removable elements, namely support stays and scapular cross straps of the multifunctional vest shown in FIGS. 1-4, in use for correcting posture and supporting thoraco-lumbar region.

Firstly, an exploded view of the posterior embodiments is shown in FIG. 5A. Two vertical thoraco-lumbar support stays 30 which can be removably attached to the garment 10, is typically manufactured from a conventional ribbed flexible material as well as other conventional resilient materials.

In addition, the two scapular straps 40 forming a posterior crossing configuration across the support stays 30, are configured to be stretchable or selectively adjustable relative to the garment 10 in a manner such that the wearer's shoulders are generally biased downwardly while the wearer's chest is generally biased outwardly. The scapular straps 40 contain two or more connectors 42, 44, 46, 48 at each end of the straps, as shown in FIGS. 1, 3 and 8, in order to adjust the tightness of the straps depending on the wearer's size and demand. The connectors 42, 44, 46, 48 are preferably of a rigid material such as metal, plastic or the like.

Further, a pair of positioning loop 26 bisected by a seam 28 into two sections that can be used for the placement of the straps 40 in a relative position across the back of the garment 10, is provided on the both side of the lower back area at the posterior portion 20.

The thoraco-lumbar support stays, scapular straps, including their connection to the shoulder and waist area are all arranged to support an upper and lower back, as well as facilitate stabilizing and correcting the posture of a wearer while in a standing or sitting position.

Figure 5B:
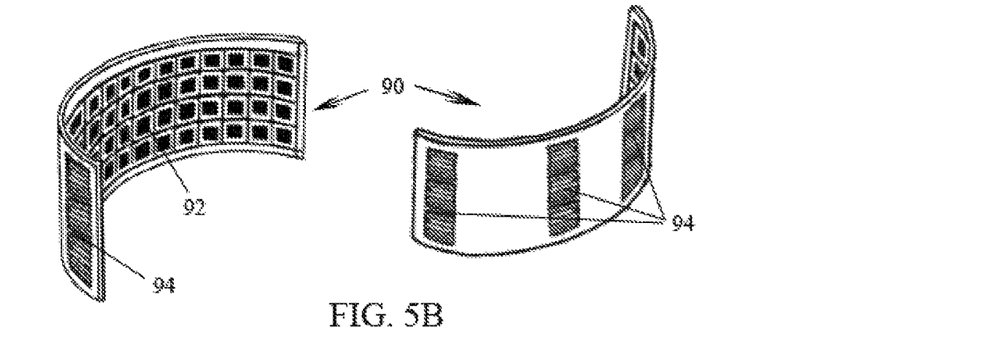
FIG. 5B is an upper perspective view of a removable element (therapeutic magnet belt) of the multifunctional vest, in use for relieving pain.
Figure 5C:
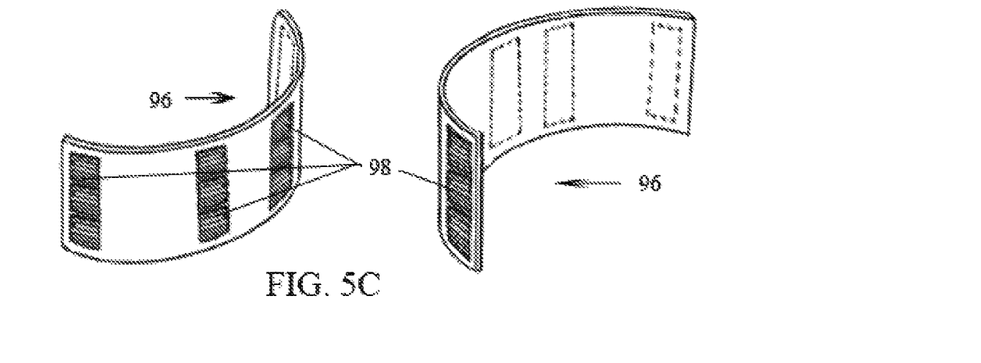
FIG. 5C is an upper perspective view of a removable element (workout boosting sheet) of the multifunctional vest shown in FIG. 5, in use for workout.

The FIGS. 5B and 5C illustrate a therapeutic magnet belt 90 and a workout boosting sheet 96 which are other preferred embodiments of the garment 10.

The therapeutic magnet belt 90 comprises of a band with a magnetic unit 92 that a plurality of magnetic blocks or sheets is distributed on the body. The band body can be made of non-elastic breathable textile or the like.

A magnetic unit 92, such as magnetic blocks or sheets, preferably, is positioned symmetrically with the spinal column and may be applied to the surface of the inner wall which faces the body of the person, provided with one or more permanent magnet arrangements producing magnetic fields directed toward the wearer's body. The permanent magnet arrangements may be provided by one or more flexible magnetic sheets received in a pocket or pockets (not shown in the example yet) on the inner wall of the band, or by permanent magnet particles embedded in the inner wall of the band and magnetized to provide desired magnetic field patterns. However, the position of magnetic unit 92 and the number of magnets are adjustable, and further, the strength of a magnet is also adjustable. Accordingly, the most convenient and effective medical treatment is obtained.

Anther embodiment, a workout boosting sheet 96 (see in FIG. 5C) is preferably composed of a breathable, somewhat elastic or non-elastic neoprene material or the like. The function of the material is to retain the part of body heat and help sweat off extra body weight while performing daily activities or doing sports.

There are multiple linear strips with hook and loop fastener 94 and 98 lining in the outer face of the therapeutic magnet belt 90 and workout boosting sheet 96 to secure the embodiments to the garment 10 where hook and loop fabrics 56 and 88 are provided. In an exemplary embodiment, the therapeutic magnet belt 90 is attached to the posterior portion 20, while the workout boosting sheet 96 is attached to the anterior portion 60. However, given embodiments can be positioned in different manner or direction from the illustrated examples. For instance, the therapeutic magnet belt 90 can be attached vertically instead of horizontally in the posterior portion 20, or switched the position with the workout boosting sheet 96 in the anterior portion 60.

Adjustable hook and loop fastener assembly 72, 74, 84, 86, an attaching configuration and method of scapular scraps 40 to the shoulder and waist area of the posterior portion 20 of the garment 10 are shown in detail in FIG. 6 in an enlarged view.

The hook and loop type fastener material is preferably VELCRO™. Other types of inter-engageable fastener devices may be provided, such as snap fasteners or the like, although "VELCRO™" is preferred since it will be more comfortable for the wearer and will provide a larger degree of adjustability and make it easier to adjust the amount of overlap between the hook and loop strips.

In an example, the hook strips 74, 86 that can have a length of about one inch or less, is disposed on the free end of the bands 70, 80, 82. The loop strips 72, 84 that can extend about 6 inches or less, is disposed on the same side of the bands 70, 80, 82 extending a significant length until the first end of the band 70, 80, 82 that stitched to the anterior portion 60 of the garment 10. The loop strips 72, 84, preferably, is more elongated than the hook strips 74, 86 so that the hook strips 74, 86 overlaps and engages, in an adjustable way.

The attachment point of the scapular straps to the body of the garment 10 is an important feature according to FIG. 6. In order to secure the scapular straps 40 to the shoulder area, pulling the free end of the shoulder band 70 at first thread through the center of connecting aperture 34 fixed at the posterior portion 20 and then through the center of connecting aperture 42 fixed in the first end of the scapular strap 40 before overlapping back onto itself, as shown in FIG. 6A. Alternatively, the additional connector 44 of the scapular strap 40 can be looped through the resultant loop formed by shoulder band 70. See FIG. 6B. In order to secure the scapular straps 40 to the waist area, pulling the free end of the waist band 80, 82 at first thread through the center of connecting aperture 36 and 38 fixed at the posterior portion 20 and then through the center of connecting aperture 46 fixed in the distal end of scapular straps 40 before overlapping back onto itself, as shown in FIG. 6C. Alternatively, the additional connector 48 of the scapular strap 40 can be looped through the resultant loop formed by waist band 80, 82. See FIG. 6D.

Referring to FIG. 7, a front exploded view of the garment 10 including the example of some embodiments with a method of utilization is described.

As apparent from the figure, the posterior embodiments are attached partially: two removable support stays 30 are sliding down until the half of the sheaths 24, a scapular strap 40 is connected with a shoulder band 70 by its first end connector 42 and with a waist band 82 by its distal end connector 46, as best shown in FIG. 6 in an enlarged view.

The anterior portion 60 is unzipped and widely opened in order to reveal the interior configuration of the garment 10. According to the figure, the anterior portion 60 is connected to the posterior portion 20 by shoulder and waist bands 70, 80, 82 in manner which of the free ends are threaded through the aperture of connectors 34, 36, 38 that fixed at the posterior portion 20 from the front to the backward direction.

Further, the free end of the shoulder and waist bands 70, 80, 82 is pulled back until the desired tightness is achieved, and then pressed against the underlying outer surface of the band itself, so that the mating hook and loop strips 72, 74 and 84, 86 are engaged. The hook and loop strips 72, 74, 84, 86 that is disposed on shoulder and waist bands 70, 80, 82 are mated together to fix the length of the bands 70, 80, 82. The hook strips 74, 86 can be removed from the loop strips 72, 84 to adjust the length of the bands 70, 80, 82 so that the anterior portion 60 is properly aligned for the individual wearing the garment 10. This forms a compact, comfortable and secure fastener of attractive appearance which can be adjusted quickly and easily as needed.

A therapeutic magnet belt 90, as best described earlier, is provided as one of preferred embodiments of the garment 10 that can provide treatment to the back and/or the torso for relieving pain and discomfort. In this embodiment, there are multiple hook strips 94 in the outer surface for attaching it to the garment 10, so that a wearer can adjust its position on demand from lower back to upper back along the linear strips with hook and loop fastener 56 provided vertically on the interior surface of the posterior portion 20.

Another preferred embodiment of the garment 10 is a workout boosting sheet 96 that keeps the body warm and heat up the core abdominal area making more sweat when a wearer doing any sports such as running, yoga or other workouts. In this embodiment, there are multiple hook strips 98 in the outer surface for attaching it to the abdominal area of the garment 10, where the linear strips with hook and loop fastener 88 are provided. Same as the therapeutic magnet belt 90, the workout boosting sheet 96 can also have alternative placement in the posterior portion 20 where the linear strips with hook and loop fastener 56 are provided.

According to the attachable embodiments mentioned above, it should be noted in FIGS. 5B and 5C, that the surface without fasteners is the inner surface which contacts the skin of the human body and the surface with hook and loop fasteners 94, 98 is the outer surface.

The plan views of the posterior portion 20 and anterior portion 60 of the garment 10 including their exterior and interior configuration are shown in FIGS. 8 and 9 in order to show the feature of the garment 10 with and without preferred embodiments.

Figure 8A:
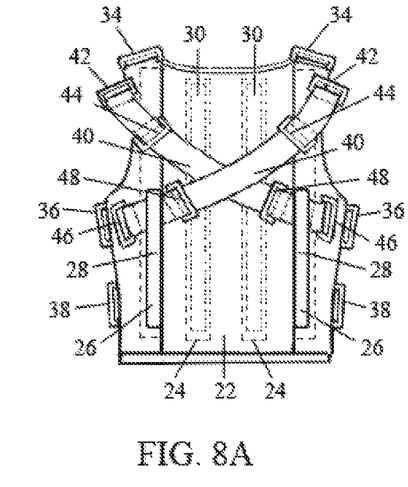
FIGS. 8A and 8B are plan views of the multifunctional vest showing its exterior configuration of the rear portion with different positions of scapular cross straps in detachable way.
Figure 8B:
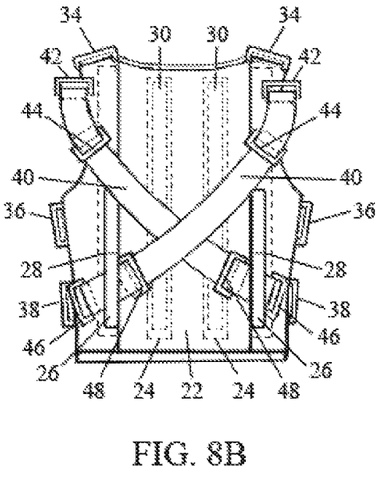

According to FIGS. 8A and 8B, scapular straps 40 can be positioned at least two different manners depending on a wearer's size and comfort of level of tightness. The scapular scraps 40 which are intended to be attached to the shoulder area by its first end connectors 42, are crossed downward the posterior panel 22 inserting through the upper resultant part of the opposite positioning loop 26, until reaching to the upper waist area by its distal end connector 46. See FIG. 8A. The distal end connector 46 of the scapular straps 40 also can be connected to the lower waist area by inserting through the lower resultant part of the positioning loop 26, as shown in FIG. 8B.

Alternatively, the scapular straps 40 can be attached to the shoulder and waist area by utilizing the additional connectors 44, 48, best seen in FIGS. 6B and 6D, if it is needed to reduce the size or increase the tightness of the straps 40 for more support on shoulders or back. Whether inserting through the upper or lower resultant part of the positioning loop 26 depends on attaching to which waist connector 36 or 38.

Figure 8C:
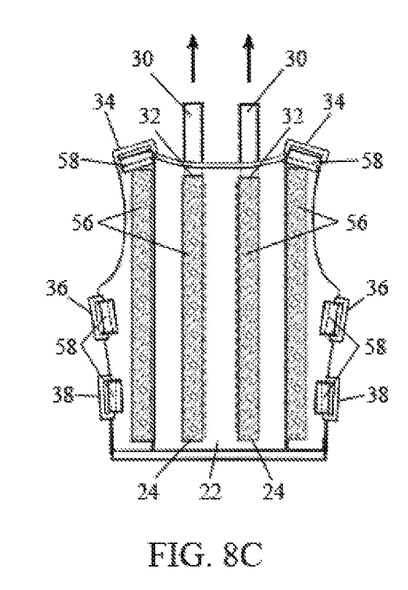
FIG. 8C is a plan view of the multifunctional vest showing its interior configuration of the rear portion with support stays inserted partially.

As shown in FIG. 8C, two elongated support stays 30 is slidably inserted into dual sheaths 24 extending between the rear neck opening 50 and hip opening 54 in posterior panel 22 of the garment 10. Each sheath 24 has a top opening 32 for insertion and removal of stays 30. The sheaths 24 closely hold the support stays 30 paramedially along each side of the spine.

Multiple connectors 34, 36, 38 are provided on the shoulder and waist area of the posterior portion 20 of the garment 10. The connector includes at least one-elongate aperture that receive fabric therein in order to secure the shoulder and waist bands 70, 80, 82. The connector is fixed to an elongate fabric holder 58 that sewn integrally on the body of the posterior portion 20.

Figure 8D:
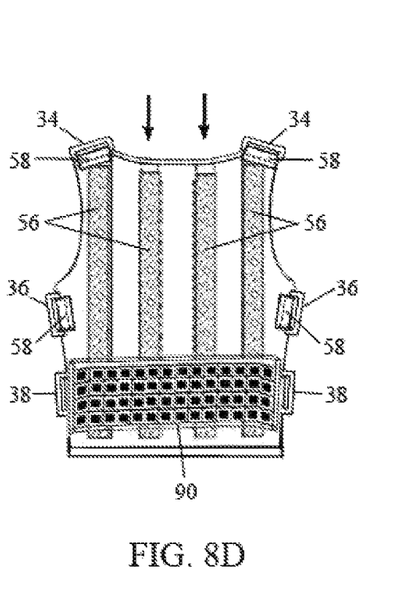
FIG. 8D is a plan view of the multifunctional vest similar to that shown in FIG. 8C but with a therapeutic magnet belt attached.

There are multiple linear strips with hook and loop fastener 56 along the back from the neck opening 50 to the hip opening 54 in the interior surface of the posterior portion 20 for attachment of given embodiments that allow a user to locate an embodiment wherever needed such as neck, upper or lower back, as well as kidney, bladder or stomach, so that magnet therapy operation can be carried out on corresponding body parts through the magnetic blocks. In an example, the therapeutic magnet belt 90 is attached in the lower back area, as shown in FIG. 8D.

With reference to FIG. 9, the garment 10 is shown its exterior and interior configuration of the anterior portion 60 with shoulder and waist bands 70, 80, 82 in an unfolded condition, at the front with an opening 76 that is closed by means of slide-fasteners, snap buttons, self-gripping device, etc. A zipper 66, in this example, forms a front closure in the anterior portion 60 of the garment 10. See also FIGS. 4 and 7.

Non-stretchable fabric fringe 78 is secured along top and side edges of the anterior portion 60 by stitching for rendering members, especially upper front section 62 substantially non-stretchable in the longitudinal direction.

A pair of shoulder bands 70 extending from the upper section 62 of the anterior portion 60 oriented towards the posterior portion 20 of the garment 10 is provided for adjusting the position of anterior portion 60 for an individual's body shape in the vertical direction.

The multiple waist bands 80, 82 are provided in the waist area extending from the waist opening 52 of the anterior portion 60 that permit adjustment of the size of the garment 10 around the girth of an individual wearing the garment 10.

One end of the shoulder and waist bands 70, 80, 82 is secured to the front neck opening 50 and/or waist opening 52 of the anterior portion 60 by stitching or the like, while the distal end is staying as a free end.

Shoulder and waist bands 70, 80, 82 include a hook and loop fastener assembly or a VELCRO™ as mentioned earlier, affixed thereto. Two lineal hook and loop strips, preferable, hook strips 74, 86 are affixed to the free end of each band 70, 80, 82, while the loop strips 72, 84 are disposed on the same side of the bands 70, 80, 82 that adjacent to the front neckline 50 and waist opening 52, respectively, as shown in these figures, as well as other figures such as FIGS. 4, 6 and 7.

Figure 9B:
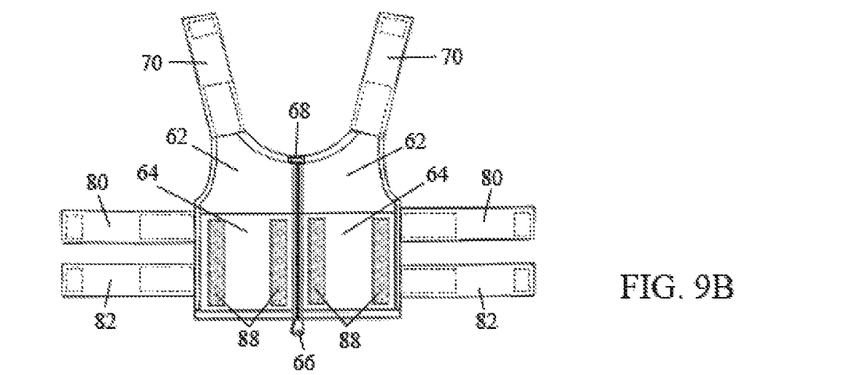
FIG. 9B is a plan view of the multifunctional vest showing its interior configuration of the front portions shown in FIG. 9A, without a removable embodiment.
Figure 9C:
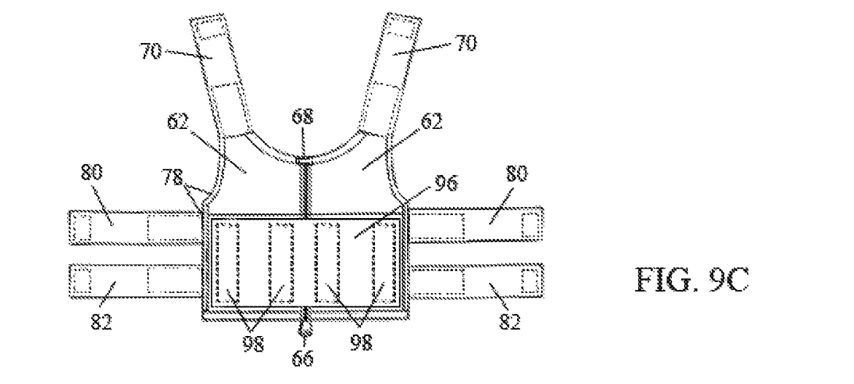
FIG. 9C is a plan view of the multifunctional vest similar to that shown in FIG. 9B but with an added workout boosting sheet.

As shown in FIGS. 9B and 9C, at the upper end of the zipper 66, it is provided with one releasably mating attachment components 68, such as hook and loop touch fasteners, conventional snaps, and conventional wire hooks and loops, etc in the inner edges of the upper section 62 of the anterior portion 60. As such fasteners are well known, a further detailed description concerning the same is not provided.

There are multiple linear strips with loop strips 88 lining vertically in the abdominal area of the garment 10 for attachment of given embodiments.

In the illustrated embodiment shown in FIG. 9C, the workout boosting sheet 96 that extends from the one side of the waist opening 52 to another covering the abdominal area, is attached. Other preferred embodiment, such as therapeutic magnet belt 90 can be attached thereto as well.

Multiple loop strips 56, 88 are lined in both posterior and anterior portion 20, 60, so that the given embodiments, such as therapeutic magnet belt 90 and workout boosting sheet 96 can be positioned in different manner or direction from the illustrated examples. For instance, the therapeutic magnet belt 90 can be attached vertically instead of horizontally in the posterior portion 20, or switched the position with the workout boosting sheet 96 in the anterior portion 60.

A multifunctional vest 100 according to the invention combines features of posture correcting device, pain relieving belt and exercise boosting garment in a single garment in male and/or female embodiments that permit freedom of movement and comfort for the user.

While the foregoing embodiments have been described and shown, it is understood that alternatives and modifications of these embodiments, such as those suggested by others, may be made to fall within the scope of the invention. Moreover, any of the principles described herein may be extended or applied to any other devices such as back protector, treatment device, exercise garment and other vest-like garments.

Further, embodiments disclosed herein are not meant to be limiting, are solely intended to offer variations of a preferred embodiment, and are not meant to exclude equivalent variations or obvious derivations of the preferred embodiment that are not disclosed herein. It is capable of other embodiments and of being practiced and carried out in various ways.

For example, the garment 10 may have long or short sleeves and/or hoodies in order to increase the utilization of the garment in different weather condition and/or other circumstances. An inner cup assembly which includes individual cups for each breast can be provided optionally for female user, too.

The shoulder and waist bands 70, 80, 82 may be switched the fixing position at the posterior portion 20 instead of the anterior portion 60 of the garment 10. Accordingly, the orientation and surface area of the hook and loop fastener assembly can be varied as desired.

The first end of the scapular straps 40 can be affixed integrally to the shoulder area while the second end remains free for adjustable connection.

Linear strips with hook and loop can be disposed either vertically, as shown in the example, or horizontally along the posterior portion 20 and anterior portion 60 as well as corresponding surface of given embodiments of the garment 10 for alternative method of attachment.

The garment 10 may have one or more connectors, clips, fasteners and the like to hold or support other objects as needed. Alternatively, two apertures connector can be used for connection.

Some embodiments such as therapeutic magnet belt 90 and/or workout boosting sheet 96 may be longer or bigger that can cover whole back area or encircle the body including abdominal and back area or may be provided multiple pieces that can apply in different parts of the body at the same time.

Different types of fabrics excluded the materials mentioned herein may be used in a single garment. The material and/or the size of the disclosed embodiments may be changed.

All in all, it will be apparent to those skilled in the art that changes and modifications may be made in the embodiments (details, materials, and arrangements of the parts) illustrated herein, without departing from the spirit and the scope of the invention. Accordingly, the invention is not limited to these embodiments or the use of elements having specific configurations and shapes as presented herein except insofar as indicated by the scope of the appended claims.

We claim:

1. A multifunctional vest for posture correcting, pain relieving and workout boosting, consisting:
    a vest-like garment extending between a neck and a hip of a wearer, said garment consisting:
        a) a posterior portion, and
        b) an anterior portion;
    two elasticized shoulder bands provided on said anterior portion and operatively connected to said posterior portion, and
    at least two or more elasticized waist bands provided on said anterior portion and operatively connected to said posterior portion,
    wherein the vest-like garment further consists of:
        a therapeutic magnet belt, and said therapeutic magnet belt consisting:
            a multiple layer band with a magnetic unit through which a plurality of magnetic blocks or sheets is distributed on the multiple layer band, and said multiple layer band can be made of non-elastic breathable textile or fabric.

2. A multifunctional vest for posture correcting, pain relieving and workout boosting as defined in claim 1, wherein:
    said posterior portion of said garment comprising:
        at least two or more connectors provided on shoulder and waist area;
    said connector includes at least one-elongate aperture that receive fabric therein in order to secure said shoulder and waist band, and
    said connector secured to an elongate fabric holder that sewn integrally on the both sides of said posterior portion, and
    said posterior portion of said garment is comprised of non-elastic breathable fabric.

3. A multifunctional vest for posture correcting, pain relieving and workout boosting as defined in claim 1, wherein:
    said anterior portion having a front closure that includes a zipper, and
    said front closure further includes a snap button to facilitate said zipper for holding closed the front opening.

4. A multifunctional vest for posture correcting, pain relieving and workout boosting as defined in claim 1, wherein:
    said anterior portion of said garment is composed of two sections: an upper section and a lower section that are integrally sewn with each other in horizontal direction;
    said upper section of said anterior portion is made of expansible material for supporting wearer's breast and chest area that is suitable for both men and women wearing;
    said lower section of said anterior portion extending below said upper section substantially to the hips of the wearer of said garment, is constructed of non-expansible material which may be same as used in said posterior portion, and
    said anterior portion having a non-stretchable fabric fringe, especially in order to keep the upper front section substantially non-stretchable in the longitudinal direction.

5. A multifunctional vest for posture correcting, pain relieving and workout boosting as defined in claim 1, wherein:
    said posterior portion and anterior portions are connected each other by said shoulder and waist bands, and
    said shoulder and/or waist band comprises a sturdy elastic material that has strong stretch.

6. A multifunctional vest for posture correcting, pain relieving and workout boosting as defined in claim 1, further comprising:
    fasteners disposed on a surface of said shoulder and waist band, and
    said fasteners are preferably a hook and loop fastener which is configured to enable engagement with each other.

7. A multifunctional vest for posture correcting, pain relieving and workout boosting as defined in claim 6, wherein:
    said hook and loop fastener comprising: two lineal hook and loop strips;
    said loop strip, preferably, is more elongated than said hook strip, so that the hook strip overlaps and engages, in an adjustable way;
    said hook strip has a length of about one inch or less, is disposed on the free end of said shoulder and waist band, and
    said loop strip has a length of about 6 inches or less, is disposed on the same side of said shoulder and waist band extending a significant length until the first end of said shoulder and waist band that stitched to said anterior portion of said garment.

8. A multifunctional vest for posture correcting, pain relieving and workout boosting as defined in claim 1, further comprising:
a pair of vertical, parallel, semi-rigid thoraco-lumbar support stays, and
said support stays are formed of plastic or other resilient material.

9. A multifunctional vest for posture correcting, pain relieving and workout boosting as defined in claim 1, further comprising:
a posterior panel extending from the neck opening until the hip opening in order to create dual, parallel sheath for holding said support stays.

10. A multifunctional vest for posture correcting, pain relieving and workout boosting as defined in claim 1, further comprising:
two flexible scapular straps extending from the shoulder area angularly downward, each strap crossing the other to form an X-shaped configuration, toward the opposite side of said garment, and
said scapular straps are made of sturdy elastic material that has a strong stretch.

11. A multifunctional vest for posture correcting, pain relieving and workout boosting as defined in claim 1, wherein:
said scapular straps having at least one connector secured at the first and distal end of said strap in order to be attached to said shoulder and waist area;
said scapular straps further having at least two or more additional connectors adjacent to each end of said straps to facilitate adjusting said straps independently depending on the size and comfort needs of the wearer, and
said connector is, preferably, a rigid material such as metal, plastic or the like.

12. A multifunctional vest for posture correcting, pain relieving and workout boosting as defined in claim 1, further comprising:
a spaced apart pair of elongate positioning loops fixedly secured to said posterior portion that helps keep said scapular straps in relative position across the back of said garment, and
said positioning loop having at least one more resultant loop created by way of stitch line that allow said scapular straps passing through and reaching to the relative (upper or lower) waist connecting position.

13. A multifunctional vest for posture correcting, pain relieving and workout boosting as defined in claim 1, wherein:
said magnetic unit, preferably, is positioned symmetrically with the spinal column and may be applied to the surface of the inner wall which faces the body of the person, provided with one or more permanent magnet arrangements producing magnetic fields directed toward the wearer's body, and/or
said permanent magnet arrangements may be provided by one or more flexible magnetic sheets received in a pocket or pockets on the inner wall of the band, or by permanent magnet particles embedded in the inner wall of the band and magnetized to provide desired magnetic field patterns, and
the position of said magnetic unit and the number of said magnetic blocks or sheets are adjustable.

14. A multifunctional vest for posture correcting, pain relieving and workout boosting as defined in claim 1, wherein:
said therapeutic magnet belt having multiple linear strips with hook and loop fastener that lining in the surface of the outer layer to secure said therapeutic magnet belt to said garment where hook and loop fabrics and are provided, and
said linear strips with hook and loop fastener is preferably hook strips.

15. A multifunctional vest for posture correcting, pain relieving and workout boosting, consisting:
a vest-like garment extending between the neck and the hip of a wearer, said garment consisting:
a) a posterior portion, and
b) an anterior portion;
two elasticized shoulder bands provided on said anterior portion and operatively connected to said posterior portion, and
at least two or more elasticized waist bands provided on said anterior portion and operatively connected to said posterior portion,
wherein the vest-like garment further consists of:
a workout boosting sheet, and said workout boosting sheet consisting:
a breathable, somewhat elastic or non-elastic neoprene material or the like that retaining the body part heat and helping sweat off extra body weight while performing daily activities or doing sports.

16. A multifunctional vest for posture correcting, pain relieving and workout boosting as defined in claim 15, wherein:
said workout boosting sheet having multiple linear strips with hook and loop fastener that lining in the outer face of the band to secure said workout boosting sheet to said garment where hook and loop fabrics and are provided, and
said linear strips with hook and loop fastener is preferably hook strips.

17. A multifunctional vest for posture correcting, pain relieving and workout boosting as defined in claim 1, wherein:
said anterior and posterior portion having multiple linear strips with hook and loop fastener in an inner surface of said anterior and posterior portion to secure said therapeutic magnet belt and workout boosting sheet to said garment;
said linear strips with hook and loop fastener is preferably loop strips, and
said linear strips can be directed either vertically or horizontally in said anterior or posterior portion.

* * * * *